(12) United States Patent
August

(10) Patent No.: US 6,503,188 B1
(45) Date of Patent: *Jan. 7, 2003

(54) ROLLABLE HEALTH CARE DISPLAYS

(75) Inventor: Joseph August, Woodstock, NY (US)

(73) Assignee: Healing Environments International, Inc., Glenford, NY (US)

( * ) Notice: Subject to any disclaimer, the term of this patent is extended or adjusted under 35 U.S.C. 154(b) by 7 days.

This patent is subject to a terminal disclaimer.

(21) Appl. No.: 09/705,481

(22) Filed: Nov. 3, 2000

Related U.S. Application Data

(63) Continuation-in-part of application No. 08/949,215, filed on Oct. 10, 1997, now Pat. No. 6,254,527, which is a continuation-in-part of application No. 08/583,473, filed on Jan. 5, 1996, now Pat. No. 5,681,259, and application No. 08/644,473, filed on May 10, 1996, now Pat. No. 5,676,633.
(60) Provisional application No. 60/163,921, filed on Nov. 5, 1999.

(30) Foreign Application Priority Data

Jun. 29, 1998 (CA) .............................................. 2241821

(51) Int. Cl.$^7$ ............................................. A61M 21/00
(52) U.S. Cl. ........................ 600/27; 160/238; 160/239; 160/327; 160/330; 160/340; 5/163; 248/466; 248/469; 248/470
(58) Field of Search ........................ 600/26–28; 40/411, 40/421; 160/10, 238, 239, 260, 327, 330, 340, 341; 5/163, 907; 248/466, 469, 470, 471, 476, 477

(56) References Cited

U.S. PATENT DOCUMENTS

| | | | | |
|---|---|---|---|---|
| 3,500,894 A | * | 3/1970 | Pofferi .......................... | 160/22 |
| 4,646,376 A | * | 3/1987 | Sulley ........................... | 5/482 |
| 5,304,112 A | * | 4/1994 | Mrklas et al. .............. | 434/236 |
| 5,400,848 A | * | 3/1995 | Gainer ..................... | 160/121.1 |
| 6,254,527 B1 | * | 7/2001 | August ........................ | 160/10 |

* cited by examiner

Primary Examiner—Rosiland S. Kearney
(74) Attorney, Agent, or Firm—Alfred M. Walker

(57) ABSTRACT

A rollable visual display is used in a room containing an article of furniture adapted to support a person, such as a bed or chair, wherein the room has a visual display support structure facing the article of furniture within the room. The visual display member, which is mounted on the support structure, is located so that when the visual display member is unfurled from the cylindrical housing, the pictorial image thereon is visible to a viewing person lying or seated in the article of furniture, wherein the pictorial image is located within the line of vision of the viewing person. Optionally, the visual display member displays a pictorial display on a surface facing the person, which is a biophilic savanna-type landscape containing imagery designed to create relaxation and reduce stress of the person.

24 Claims, 4 Drawing Sheets

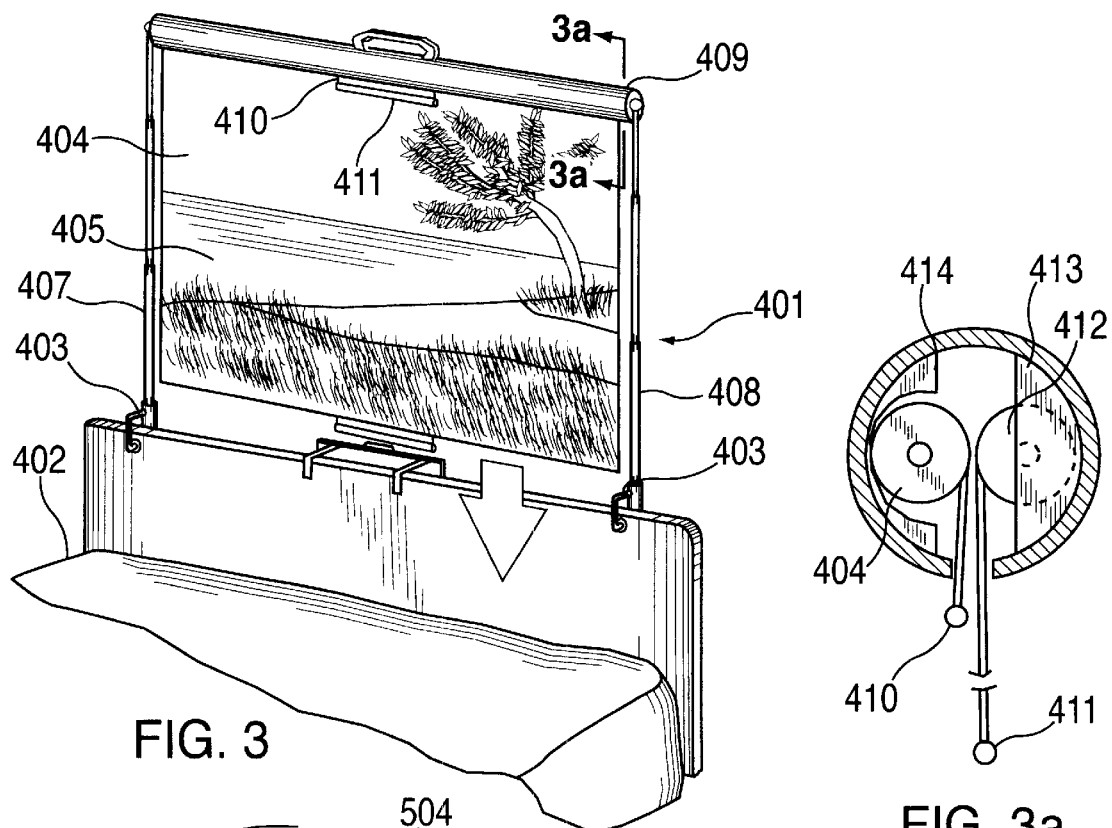
FIG. 3
FIG. 3a
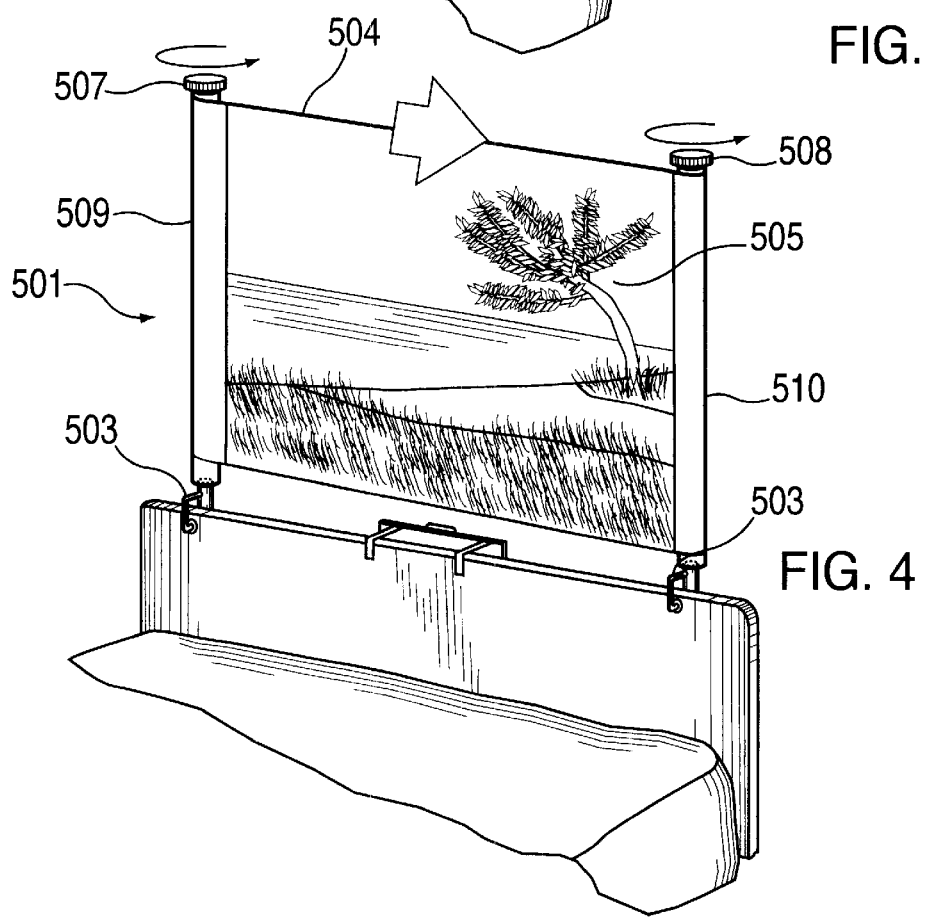
FIG. 4

ROLLABLE HEALTH CARE DISPLAYS

RELATED APPLICATIONS

This application is a continuation-in-part of my patent application Ser. No. 08/949,215, filed Oct. 10, 1997 U.S. Pat. No. 6,254,527 which application is a continuation in-part of application Ser. No. 08/583,473, filed Jan. 5, 1996, now U.S. Pat. No. 5,681,259 dated Oct. 28, 1997, and application Ser. No. 08/644,473, filed May 10, 1996, now U.S. Pat. No. 5,676,633 dated Oct. 14, 1997. This application is also based upon my provisional patent application No. 60/163,921 filed Nov. 5, 1999.

FIELD OF THE INVENTION

The present invention relates to an apparatus for promoting personal relaxation and reducing stress in an environmentally stressful setting, such as a health care or other setting.

INCORPORATION BY REFERENCE

The disclosures of my U.S. Pat. Nos. 5,676,633 and 5,681,259 and my pending applications are incorporated by reference thereto.

For example, my aforesaid U.S. Pat. Nos. 5,676,633 and 5,681,259 are directed to a method and apparatus for biophilically promoting patient relaxation, for reducing physical and/or psychological patient stress and for expediting patient recovery. More particularly, my patents describe and apparatuses used to expose persons to appropriately selected visual stimuli which promote induce relaxation and reduce stress, as well as promote patient recovery in intimate settings in hospital room environments and like settings.

My prior patents are also related to a method of relaxing a patient in a health care, hospital or convalescent setting, by providing a patient with a choice of selecting for viewing one or more high resolution spatially open, serene natural landscape scenes to which the patient is believed to have an innate positive (biophilic) affinity, upon a fabric frame display member mounted upon a flexible wall partition, such as a hospital curtain. In one embodiment, the spatially open, serene natural landscape scene is a savanna-type landscape or a like scene to which humans are believed to have a biophilic affinity.

A biophilic landscape picture is printed preferably on a flexible fabric by a high resolution sublimation printing process, wherein an image is first scanned into a computer and then transformed by state-of-the-art technology to the fabric, such as described in the "Background of the Invention" herein. The image may also be printed directly on all or a portion of a hospital curtain itself.

My prior patents also discuss that because of hospital safety protocol and safety codes (such as what is referred to as "National Fire Protection Association (NFPA) 701" codes), the fabric must either be inherently flame retardant or specially treated to meet protocol or code requirements. Moreover, in accord with hospital sanitary protocol, the fabric sheet pieces and inks thereon should be washable and durable to heated washing standards of 160 degrees F. so that any infectious organisms thereon are eradicated.

The patents also note that such printing produces substantially glare-free photorealistic images of sufficient size (e.g. four by five feet) to give the patient the perception of actually being in a natural (i.e., biophilic) setting. Printing the photorealistic image is accomplished on inherently fire retardant or treated fabric in a manner that upholds the post-printing fire retardancy of the fabric and that enables the fabric to be laundered and disinfected at the required high water and drying temperatures required by hospital sanitary codes and standards without substantially degrading the image quality of the picture. On a reverse side of the fabric one or more fastening means, such as strips of hook-and-loop-type fasteners, sold under the trade name of VELCRO®, are attached. Corresponding strips of hook-and-loop type fasteners are attached to a portion of a hospital room curtain which at least partly encloses a hospital patient's bed. Other conventional fasteners such as snaps, safety pins, clips, etc., may be substituted or additionally employed.

My prior patents also disclose that by attaching the fabric picture to the patient-facing side of the hospital curtain, the biophilic landscape picture can remain visible to the targeted patient in the bed even when the curtain is contracted. During visiting hours, when the curtain is normally partially expanded, the landscape picture can be left visible on a portion of the curtain.

My patents also discuss that the biophilic picture should be within the person's line of vision. In conjunction with exposure of the patient to the spatially open, serene natural landscape picture, the patient may be provided with soothing natural sounds appropriate to the landscape picture and/or mild aromatic odors reminiscent of natural aromas associated with the landscape picture.

In selecting a spatially open, serene natural landscape for the patient to view, it is important that the patient not be exposed to over-exciting or anxiety producing landscape scenes, (which may unconsciously raise the stress level of the patient and/or may affect the visual and auditory nerve balance mechanisms of the patient).

Therefore, selection of the biophilic visual image to be conveyed to the patient preferably encompasses selection of spatially open, serene landscape scenes which are substantially the same as, or similar to, the archetypal savanna-type landscape scenes, suggested by Ulrich, Wilson and other scientific authorities on biophilia.

My patents further note that the subjects of a biophilic scene, or other spatially open, serene, natural landscapes must be carefully chosen and the natural scenes should be selected in relation to the most recent relevant environmental psychology research (such as defined by Ulrich). Although pre-dating both the 1984 seminal work by Wilson and the subsequent 1993 publication of Ulrich, an example of environmental psychology methodology research on differential human perceptions of varying outdoor scenes is the 1974 work of Shafer and Richards entitled "A Comparison of Viewer Reactions to Outdoor Scenes and Photographs of These Scenes", (Shafer et al., 1974, U.S. Dept. of Agriculture, Forest Service Research Paper No. NE-302, Northeastern Forest Experiment Station, Forest Service, U.S.D.A., Upper Darby, Pa.)

In the Shafer and Richards study, eight different types of outdoor scenes were shown to viewers in three different modes: (i) on-site viewing of the actual scenes; (ii) viewing color transparencies of the scenes; and (iii) viewing color photographic prints of the scenes. Viewer responses to each scene were compared statistically and geographically to determine which outdoor scenes had more positive effects on the viewers.

My patents discuss that upon selection of the picture to be displayed to the patient, it should be conveniently displayed, such as on the hospital curtain, as noted before. However, other embodiments of the present invention include other visual display means not previously described in this application. One such other kind of embodiment is a wall or ceiling mountable, roll-up-able and roll-down-able screen depicting a spatially open, serene natural landscape scene (preferably a biophilic savanna-type scene).

Unlike the generalized nature photography described in U.S. Pat. No. 4,763,428 of Fischer, which describes providing a nature scene in a hospital wall-mounted picture frame, and the Fischer "Visual Therapy" publication, the present invention applies the latest research findings and theory in the behavioral and natural sciences to the selection and installation of appropriate nature photography scenes in hospital rooms and other convalescent settings. It does so in a manner that creates a simulated natural environment to promote the hospitalized patient's recovery.

The selection of healing and recovery-promoting natural landscape scenes requires knowledge of the latest research findings concerning the health effects of viewing biophilic nature scenes, since not all natural landscape scenes have a therapeutic affect. In fact, uninformed, improper or inappropriate picture selection has been shown to have deleterious effects on patients, disturbing them rather than promoting their healing.

My patents also note that what is essential in the selection process is that the visual stimuli not merely tend to "involve, distract and occupy the attention of the viewer" but that such elicited patient responses promote the patient's healing and recovery. The present invention reflects an understanding of how to stimulate such viewer-based recovery responses because it is based on a firm foundation of the latest research findings and theoretical research focusing on the biophilic effects of viewing nature on human health outcomes.

This research, by Wilson, Heerwagen, Orians, and Ulrich et al informs the user of the appropriate method of selection of recovery-promoting biophilic natural landscape scenes. Merely placing a picture on a hospital room wall whether in a frame, a light box or a video screen, is not sufficient to promote patient recovery. The Fischer '428 background art on hospital room walls is located at too remote a distance from the patient to promote the patient's perception of being in the environment represented by the picture. Moreover, while the Fischer "Visual Therapy" publication describes the lighted depiction of large photographs from light boxes or video screens, the light emitting features of the light boxes or video screens may produce unwanted optical glare. Furthermore, viewing of wall mounted light boxes and video screens can be obstructed by fabric hospital curtains drawn between a patient and a hospital room wall.

Therefore, the subject matter of my prior patents is distinguished from the background art by providing very large sized high resolution photo realistic biophilic natural landscape scenes that, by being printed on flexible fabric, enable these scenes to be removably mounted on the patient's bedside cubicle privacy curtain in the patient's direct line-of-sight at the foot of the bed, thereby providing the patient with an immediately close-up simulated natural visual environment. Since wall-mounted art described in the background art has the disadvantage of being obscured from the patient's view whenever the cubicle curtain is drawn to provide privacy to the patient, the patient is therefore caused to have to choose to either have personal privacy or to be able to view the wall-mounted photography.

With the above-described embodiment of my issued patents, the person no longer has to suffer the above described dilemma. It provides the patient with an opportunity to choose one or more pre-selected biophilic scenes that, by virtue of their placement on the cubicle curtain, can be viewed at the discretion of the patient any hour of the day or night without the glare of a video screen or the remoteness of a wall mounted frame. With the embodiment of the present invention the patient is not forced to choose between having personal privacy or viewing wall-mounted nature photography. On the contrary, with this embodiment of the present invention the patient is able to enjoy the benefit of (or exercise the choice of having) personal privacy while simultaneously having the opportunity to view selected restorative biophilic nature photography.

My patents also disclose that an additional embodiment of the latter-described embodiment augments the visual dimension of the environment with complementary audio recordings of biophilic sounds appropriate and specific to each scene. Still another embodiment augments the visual and audio stimuli with aromatic scents that are appropriate and specific to each scene. Also, the method of the present invention may allow (after a set of spatially open serene natural landscape scenes is selected by the patient's care giver) the patient to select one or more of these scenes. This alternative variation permits patients to exercise choice, thereby improving the patient's self-efficacy and ultimate recovery.

Moreover, the biophilic or other spatially open, natural serene landscape scenes may be visually displayed substantially glare-free in other medical or convalescent environments, such as in the offices of health practitioners, (e.g., physicians, dentists, acupuncturists, chiropractors, and physical therapists). Other appropriate settings include diagnostic rooms at hospitals, adult day care centers, other institutional settings and/or at a private residence (such as where an infirm person might be confined to a particular room for extending periods of time while recovering from illness or surgery).

Structurally, my prior patents describe a biophilic landscape image on a flexible fabric display, or a roll-up-able and roll-down-able device for displaying another spatially open natural landscape image. A further alternate embodiment discloses a ceiling mounted-biophilic landscape image.

In summary, my prior patents describe a method of biophilically promoting patient welfare, by exposing a patient to a preferably conveniently mounted, substantially optically glare-free biophilic pictorial landscape image to which human beings are believed to be generally genetically predisposed to viewing favorably, so as to biophilically induce relaxation, reduce stress and/or promote post-surgical recovery. The beneficial effects of providing the landscapes image may be augmented by providing the patient with soothing natural sounds or aromas. Display materials, having a biophilic pictorial landscape image affixed thereto by substantially glare-free high resolution sublimation printing, can be removably or changeably mounted as a convenient removable flexible and lightweight display member, to a hospital curtain or other structure so as to substantially maximize exposure of a patient to the biophilic image in an intimate, substantially glare-free environment. It is also important that the pictures be removable, so that the patient can exercise choice in selecting the picture to be viewed, and thereby improve the patient's self efficacy and self esteem.

In addition to my two prior patents noted above, I incorporate by reference the subject matter of my pending continuation-in-part patent application filed under Ser. No. 09/949,215 of Oct. 10, 1997, which describes an unframed, freely suspended visual display member of fire retardant fabric construction to eliminate glare, which is mounted loosely on the support structure and which displays a biophilic savanna type landscape upon a fabric visual display member in a setting to promote relaxation and reduce stress.

The visual display member is an unframed, freely suspended visual display member of fire retardant fabric construction to eliminate glare being mounted loosely on the support structure. As shown in my drawing Figures therein, the visual display member is not in a rigid picture frame of a scene, which cannot be freely suspended from the support structure, such as the self-standing mounting stand shown in FIGS. 9–16 in that application.

In contrast, the fabric visual display member of my pending continuation-in-part application is an unframed, freely suspended visual display member that is mounted loosely on the support structure, such as the self standing mounting stand. It is draped loosely, and is not mounted rigidly within a rigid frame as in Fischer.

My pending continuation-in-part also discloses a visual display member with an image upon the fabric display being a savanna type landscape and optionally that the display member is of a fire retardant fabric, wherein the printing thereon is produced on the fire retardant fabric by a high resolution sublimation printing process resulting in said display and fire retardant fabric being washable and durable to heated washing standards of 160 degrees F. so that any infectious organisms thereon are eradicated.

Such features are described in my issued U.S. patents, with the exception that the setting is not limited to a hospital setting and that the display member is freely suspended and loosely mounted upon the support structure. My pending continuation-in-part also describes the imagery as being designed to create relaxation and reduce stress of said person, wherein the biophilic landscape imagery suggests environments in which the evolutionary differentiation of Homo sapiens from ancestral paleoanthropopids is believed to have occurred and wherein the biophilic landscape imagery includes imagery of vegetation dominated by a relatively low herbaceous understory and a relatively widely spaced tree canopy.

Such an anthropologically defined class of biophilic imagery is well thought-out and discussed in detail in the specification at pages 1–3 and 15–18 of my pending continuation-in-part application.

My pending continuation-in-part also notes imagery which is designed to create relaxation and reduce stress of said person, wherein the biophilic landscape imagery suggests environments in which the evolutionary differentiation of Homo sapiens from ancestral paleoanthropopids is believed to have occurred and wherein the biophilic landscape imagery includes imagery of vegetation dominated by a relatively low herbaceous understory and a relatively widely spaced tree canopy.

My pending continuation-in-part also describes the use of any kind of fastener for fastening such a visual display upon a curtain, such as grommets, hooks, etc. and the like, in addition to the hook and loop fasteners disclosed in my two issued patents.

BACKGROUND OF THE INVENTION

Positive psychological and physiological responses are elicited in humans by visual exposure to pleasing landscape images such as pictures of spatially open natural landscapes. (Roger S. Ulrich, 1993, "Biophilia, Biophobia and Natural Landscapes", Chapter 3, pages 73–137, in: Stephen R. Kellert and Edward O. Wilson editors, The Biophilia Hypothesis, Island Press, Washington, D.C.). The preferred landscape image is a savanna-type landscape. By definition, a savanna-type landscape is a "grassland with scattered trees or scattered clumps of trees, a type of community intermediate between grassland and forest" (Eugene P. Odum, 1971, Fundamentals of Ecology, Third Edition, W. B. Saunders Company, Philadelphia, Pa.).

In one of his seminal and theoretical works, renowned evolutionary biologist Edward O. Wilson (1984), Biophilia: The Human Bond with Other Species, Harvard University Press, Cambridge, Mass.) suggests that humans are genetically predisposed to respond positively (biophilically) to savanna-like landscapes. After the publication of Wilson's seminal work on island biogeography (Robert H. MacArthur and Edward O. Wilson, 1967, The Theory of Island Biogeography, Princeton University Press, Princeton, N.J.) and his expansive synthesis on sociobiology (Edward O. Wilson, 1975, Sociobiology: The New Synthesis, Harvard University Press, Cambridge, Mass.), biologists and others wrote many papers, dissertations and books on these topics of modern bioscience. Like the responses by the bioscientific community to his 1967 and 1975 works, Wilson's 1984 publication of Biophilia: The Human Bond with Other Species has prompted the writing of many scientific papers by a wide diversity of authorities. Among these works on biophilia are two papers especially relevant to the present invention: the aforecited "Biophilia, Biophobia and Natural Landscapes" by Ulrich, and "Humans, Habitats, and Aesthetics" by Judith H. Heerwagen and Gordon H. Orians (1993, Chapter 4, pages 138–172, in Stephen R. Kellert and Edward O. Wilson, editors, The Biophilia Hypothesis, Island Press, Washington, D.C.).

The biophilic theory of Wilson supports the belief that natural selection favored the survival of paleohominids (ancestors of modern humans, Homo sapiens) genetically predisposed to inhabiting landscapes dominated by plant life forming vegetation having a physiognomy of a savanna. Such ancestral hominids are viewed as having innate aversions to desert, densely forested and like landscapes generally less favorable to paleohominid survival than savannas. Human evolution is believed to have occurred substantially within tropical savannas in Africa. Predation, food-availability and other selection pressures were generally more favorable to human survival and evolution within these tropical savannas than in other kinds of African landscapes (such as tropical rain forest, mountainous, desert and like environments). Selection promoted disproportionately high survival of hominids and hominid genes favoring savanna-oriented behaviors. As evolution proceeded, there was a build-up and strengthening of genes and gene-combinations further predisposing hominid populations to savanna conditions. Wilson believes that these innate savanna-oriented characteristics continue in populations of modern humans and that modern humans are biophilically predisposed to responding favorably to savanna or savanna-like conditions. Certain embodiments of the present invention are in accord with this belief of one of the most widely respected and acclaimed biologists in the world today.

In the aforementioned 1993 publication of Ulrich, Ulrich reports evidence that simulations (including color photographs) of natural environments elicit restorative and other positive responses from human viewers and suggests that such simulations may serve as at least partial substitutes for real nature in terms of eliciting short-term restorative responses. Other scientific authorities are mentioned by Ulrich as providing proof that the viewing of natural settings positively affects the viewer by reducing stress (confirmed by such central nervous system indicators as blood pressure). This reporting by Ulrich is consistent with the innate biophilic landscape affinity believed by Wilson to characterize modern humans. The work of Ulrich suggests that positive (biophilic) responses can be elicited from patients within a very short time after patient exposure to wall art showing spatially open serene natural settings.

However, most attempts to reduce stress in a hospital or therapeutic setting have been sound-oriented, wherein music or other sounds are electronically delivered to a patient. Where visual images are used to address patient well being, the images are either displayed remotely in a far away picture frame, or in optically glare-producing video screens.

The most relevant patents are U.S. Pat. No. 5,403,263 of Rodgers, for a method of reducing the recovery time and stress associated with surgery and U.S. Pat. No. 4,763,428 of Fischer for providing a nature scene in a hospital wall-mounted picture frame. Rodgers '263 describes a method to reduce hospital recovery time and stress by providing verbal voice-over suggestions and soothing anxiolytic music before, during and after surgery. Fischer '428 describes the use of wall mounted pictures to assist in patient healing, but does not focus on what pictures to select other than nature scenes in general.

Weisz (U.S. Pat. No. 3,140,709) describes a pain relieving apparatus wherein acoustical sounds such as music are fed through ear phones to divert a patient's attention from pain.

Rabichev et al. (U.S. Pat. No. 3,773,049) describe an electronic apparatus for treating neuropsychic and somatic disorders with repetitive exposure of the patient to light, heat and sound radiation sources.

Banks (U.S. Pat. No. 4,047,377) discloses an electronic sleep promotion apparatus wherein a wide band audio frequency generator applies audio impulses to a person.

Chang et al. (U.S. Pat. No. 4,082,918) describe an electronic audio device which provides analgesic sounds to dental patients.

Gross (U.S. Pat. No. 4,124,022) describes an electronic audio speaker in the shape of a heart, which provides repetitive slow heartbeat sounds, to relax a person.

Kashar (U.S. Pat. No. 3,643,941) describes a relaxation chamber containing a plurality of STYROFOAM® balls to simulate movement of a person within a swimming pool. Colored lights are projected upon the STYROFOAM® balls to enhance the person's relaxation.

Adams (U.S. Pat. No. 3,826,250) discloses a relaxation chamber including a lounge chair wherein lights and sounds are electronically provided to a resting person.

Steigler (U.S. Pat. No. 4,553,534) describes a stress-reducing helmet with an eye shield, wherein electronic images and sounds are transmitted to the wearer.

Warnke (U.S. Pat. No. 4,573,449) describes a method for sleep enhancement and/or relaxation wherein a headphone generates electronic sound pulses, which are provided to an insomniac person to induce sleep.

Lawson (U.S. Pat. No. 4,640,267) and Cuervo (U.S. Pat. No. 4,681,096) both describe methods and associated devices to abate an infant's crying, wherein electronic sounds or vibrations are scheduled for repetitive introduction to the infant.

Gall (U.S. Pat. No. 5,289,438) discloses a consciousness-altering apparatus for persons, wherein multiple sound stimuli are electronically provided to a person.

Monroe (U.S. Pat. No. 5,356,368) describes a method and apparatus for altering consciousness and inducing sleep by measuring electroencephalogram (EEG) brain wave forms of a person during sleep or relaxation, and using sounds to try and reproduce the sleep inducing or relaxation-inducing brain waves of the person.

Dillinger (U.S. Pat. No. 5,377,024) describes an electronic color forming image construction device.

Spiegel (U.S. Pat. No. 5,425,699) describes the use of electronically produced sound waves to induce hypnosis in a person.

Okuda (U.S. Pat. No. 4,762,131) discloses an electronic nerve stimulation including lights and sounds to treat paralytic patients.

Monroe et al. (U.S. Pat. No. 5,356,368) describe a method for predicting when a night-shift worker might lose alertness.

Saperston (U.S. Pat. No. 5,267,942) discloses the use of electronically generated sounds to monitor optimal target heart rates in persons.

Davis (U.S. Pat. No. 5,352,181) describes a method and apparatus for inducing relaxation by providing verbal and musical sounds in ascending and descending crescendos and phases, to stimulate relaxing alpha and beta brain waves.

However, Rodgers '263 and most of the above noted background art patents are directed to electronic sound generating devices to induce relaxation states in users. Some of these devices, such as the embodiments of Okuda '131 and Kashar '941, involve the use of electronically generated flashing lights to induce relaxing states of mind.

Furthermore, providing such a repetitive exposure of a patient to music, sounds and/or flashing lights has the disadvantage of being expensive to install and also may overstimulate the patient.

Moreover, these background art devices do not describe a method and apparatus for providing biophilic landscape images to hospital patients to promote recovery. Furthermore, the hospital room environment itself has the disadvantage of discouraging exposure of persons to pictures in general, because slidable fabric curtains are often drawn around the patient's bed, thereby hiding any wall-mounted pictures, such as described in U.S. Pat. No. 4,763,428 of Fisher, from the patient's view.

Fischer also discloses in an unpatented publication entitled "Visual Therapy" the displaying of one of many nature photography scenes in a light box or a lighted electronic video screen in a health care setting. However, the lighted images are subject to optical glare. The background art of Fischer '428 and the Fischer "Visual Therapy" publication of visually oriented approaches to patient well being is aimed primarily at providing either a reusable lockable means, such as a picture frame, or a light box or video screen, to display pictures that are only generally described as "having a therapeutic value", and "particularly well suited to visually involve, distract and occupy the attention of the viewer" of nature photography on the hospital room wall. There is no specificity as to the theoretical basis for selection of the nature photography; nor are any selection guidelines presented.

While a hospital curtain exhibits a large, convenient surface upon which to display pictures, curtains have not been generally used to display framed pictures, because the weight of a picture frame may distort the curtain and/or because the rigid picture frame may be a hazardous hindrance obstructing egress in the vicinity of the curtain. In addition, light boxes and lighted video screens present other electricity related hazards.

Therefore, there is a need for a lightweight, flexible display means for pictures, which can be attached to a hospital curtain without distorting the curtain and without obstructing egress to the patient in the vicinity of the curtain.

In fact, flexible removable pictures have mainly been provided within infant cribs to protect an infant's safety, as noted in U.S. Pat. Nos. 5,307,574 and 5,125,175 of Huff.

Moreover, imprinted photographic pictures cannot normally be displayed on fabrics, such as curtains, because the images fade with repeated washing of the fabric materials.

The technical challenges in providing such cubicle curtain-mounted images include (1): Any fabric that is used must either be inherently fire retardant or specially topically treated to meet the fire retardancy standards as set forth in National Fire Protection Association (i.e., NFPA) Code 701. (2) The printing must produce images of sufficient high-resolution photo-realism and sufficient size (e.g., four by five feet) to give the patient the perception of actually being in a natural (i.e., biophilic-like) setting. (3) The photo-realistic image must be printed on inherently fire retardant or treated fabric, in a manner that upholds the post-printing fire retardancy of the fabric and in a manner that enables the fabric to be laundered and disinfected at the high water and drying temperatures required by hospital sanitary codes and standards while maintaining the image quality of the picture.

High resolution, non-fading printing of photographic images on cloth fabrics may be obtained by special printing processes, such as, for example, sublimation printing. Sublimation printing produces images which have high image resolution with much clarity and brilliance, without the visually disturbing effects of glare produced by light boxes or electronic screens, such as described in the Fischer "Visual Therapy" publication.

Among the background art describing sublimation printing include U.S. Pat. Nos. 5,460,871 of Andersen, 5,441,997 of Walsh, 5,389,493 of Asai, 5,329,381 of Payne, 4,997,506 of Recher, and 4,804,977 of Long.

In sublimation printing, the coloring agents are subliminally transferred to the fabric. Sublimation printers use sublimation powders or printer ribbons to produce heat transfers, which release sublimation inks in a wide variety of distinctive colors, as noted in U.S. Pat. No. 5,281,499 of Bussard.

Since the resolution quality is achieved with photographic images printed on fabrics by sublimation printing, the fabrics can therefore be fire retardant and washable, so that the fabrics can be laundered and disinfected when washed at high water temperatures with cleaning products.

Reusable fabrics are also much easier to clean and maintain than complicated light boxes or electronic video screens, and are more easily interchangeable than heavy, wall mounted picture frames.

Therefore, the high water temperatures and cleaning products (which are needed to bring fabrics up to hospital and other sanitary codes,) do not substantially diminish the high resolution and clarity of photographic images produced by sublimation printing upon a fabric, such as hospital curtain material or another suitable fabric attachable to a hospital curtain. Moreover, these cleaning methods do not diminish the fire retardancy of the inherently fire retardant fabric.

OBJECTS AND SUMMARY OF THE INVENTION

The present invention includes a rollable visual display to be used in a room containing an article of furniture adapted to support a person, such as a bed or chair, wherein the room has a visual display support structure facing the article of furniture within the room.

The visual display member is mounted on the support structure.

The visual display member is located so that when the rollable visual display member is unfurled from within the cylindrical housing, the pictorial image thereon is visible to a viewing person lying or seated in the article of furniture, wherein the pictorial image is located within the line of vision of the viewing person.

Preferably, the visual display member has a pictorial display on a surface facing the person, which is a biophilic savanna-type landscape containing imagery designed to create relaxation and reduce stress of the person. Preferably it is attached to the person's bed for ready removal of the fabric visual display member to and from the support structure. Removal can be achieved by clamp or other conventional quick release fastener.

For a bed mounted unit, the support structure includes a top handle for pulling a cylindrical container housing for accommodating rollable visual displays therein. The cylindrical housing holding the visual display units is supported up on telescopic poles, which are attached to a bed frame and which increase in height telescopically.

There are also handles for pulling each respective pictorial display downwards and unfurling the visual display from the upper cylindrical housing.

Each visual display unit is modular and interchangeable, so as to fit and snap into quick release points on each side of the cylindrical housing. The pictorial display are rolls, which roll into the cylindrical housing. The cylindrical housing may have half walls on either end to serve as a mounting points for the pictorial display rolls.

Preferably two or more visual display rolls may be mounted side by side inside the bed mounted cylindrical housing, which may be made of a suitable material such as, for example, plastic or metal.

An alternative embodiment has a horizontally oriented scroll-type arrangement, wherein the pictorial display rolls move horizontally in a bed-mounted unit and the plurality of pictorial displays are held in place within vertically upstanding housings on either side of the bed frame.

Handles are provided for pulling the pictorial displays downwards. This wall mounted unit can be mounted by a wood screw which attaches through sheet rock panels into wall studs, or a molly fastener can be used to support the wall mounted unit. These "window shade" style pictorial displays are in individual compartments until pulled down to be displayed.

In the preferred embodiments, the apparatus' of the present invention can be used to provide a method of relaxing a person in a stressful environment, such as a patient in a healthcare, hospital or convalescent setting, by providing the person with a choice of selecting for viewing one or more spatially open, serene natural pictorial landscape scenes to which the person is believed to have an innate positive biophilic affinity, upon a conveniently viewable display, such as the bed or wall mounted surface In the preferred embodiments, the spatially open, serene natural landscape scene is a savanna-type landscape or a like scene to which humans are believed to have a biophilic affinity.

In the bed or wall mounted environment, by exposing the pictorial display to the viewer, the biophilic landscape picture can remain visible to the viewer in a bed or chair.

Preferably, in the bed mounted version, the pictorial display is attached so that it is visible at the foot of the patient's bed, within the patient's line of vision.

Upon selection of the picture to be displayed to the patient, it is conveniently displayed, such as on the bed or wall mounted display.

Unlike the generalized nature photography, the preferred embodiments of the present invention apply the latest research findings and theory in the behavioral and natural sciences to the selection and installation of appropriate natural scenes in stressful environments, such as the hospital room and other settings, such as healthcare or educational institutions, hospitality accommodations, office cubicles or waiting rooms. It does so in a manner that creates a simulated natural environment to reduce stress and to promote the person's relaxation.

The selection of healing and recovery-promoting natural landscape scenes requires knowledge of the latest research findings concerning the health effects of viewing biophilic nature scenes, since not all natural landscape scenes have a therapeutic affect. For example, harsh alpine mountain settings or vigorous ocean wave settings may unnecessarily provoke stress in a person, or visually disturb a recovering patient's vestibular balance.

Alternatively, additional optional embodiments include complementary audio recordings of biophilic sounds appropriate to the visual display, such as gently falling water or chirping birds, may be provided. Still another embodiment includes providing aromatic scents that are appropriate to the visual display.

What is essential in the selection process is that the visual stimuli not merely involve, distract and occupy the attention of the viewer but that exposure to the bed or wall mounted pictorial displays promote the patient's healing and recovery.

DESCRIPTION OF THE DRAWINGS

The present invention can best be understood in conjunction with the accompanying drawings, in which:

FIG. 3 is a perspective view showing a biophilic image thereon;

FIG. 3A is a cross sectional view of the display on FIG. 3, taken along lines "3a—3a" of FIG. 3;

FIG. 4 shows an alternate scroll type bed mounted visual display;

DETAILED DESCRIPTION OF THE DRAWINGS

Figure 1:
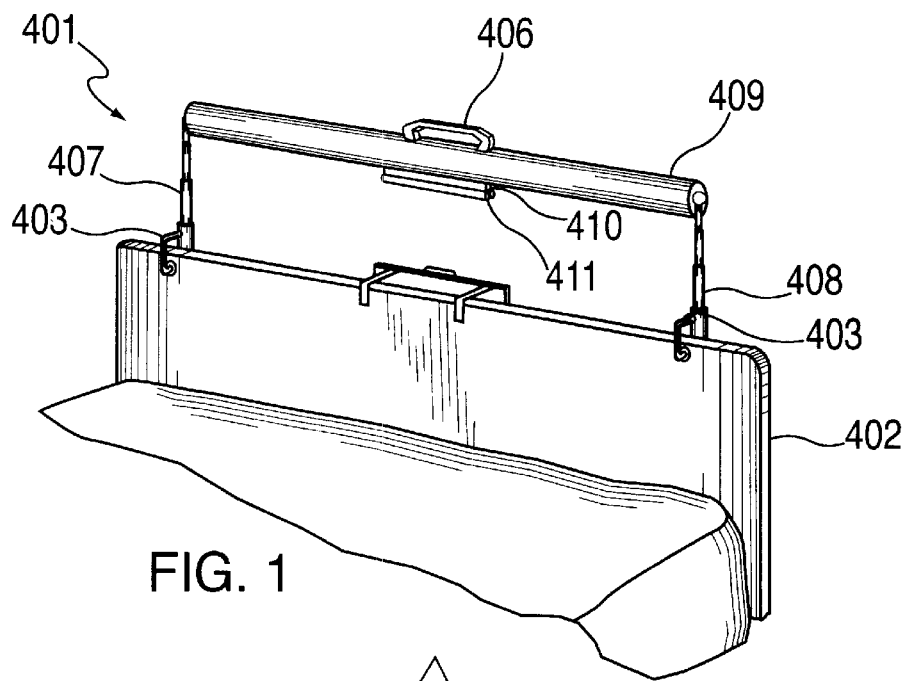
FIG. 1 is a perspective view of the bed mounted visual display of one embodiment of the present invention, shown in the partially extendible position.
Figure 2:
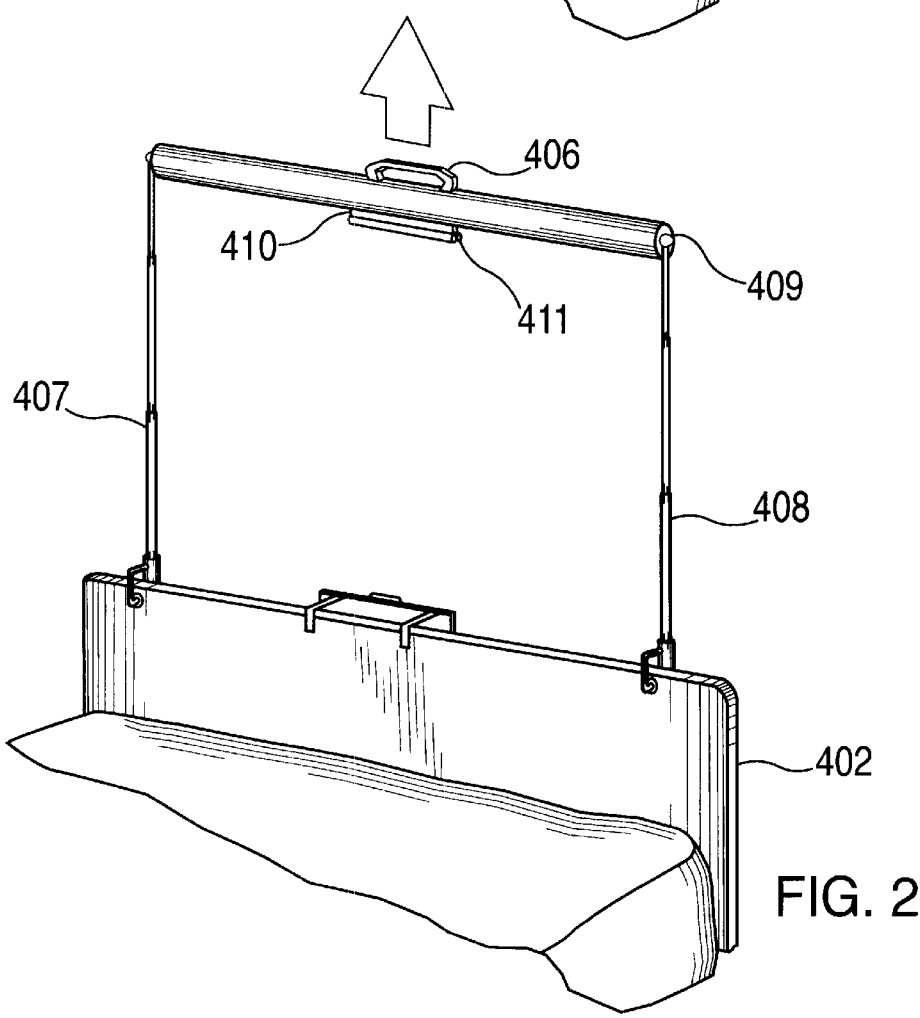
FIG. 2 is a perspective view of the bed mounted display as in FIG. 1, shown in the fully extendible, viewing position.

As shown in FIGS. 1, 2, 3 and 3a, the present invention includes an apparatus 401 for promoting personal relaxation and reducing stress in an environmentally stressful setting, such as a hospital room.

It is used in a room containing an article of furniture, such as bed 402 adapted to support a person, wherein the bed 402 has one or more support structures 403 facing the bed 402 within the room. Support structures 403 may be clamps or quick release fasteners attachable to the bed frame of bed 402.

A visual display member 404 of fabric or rollable paper or fabric construction (made sanitary and fireproof according to hospital safety standards) is mounted on the support structures 403. A plurality of visual display members 404 and 412 may be provided as well.

The visual display member 404 is located so that the visual display member 404 is visible in the vicinity of the bed 402 within the line of vision of the viewer.

The visual display member 404 has a pictorial display 405 on a surface facing the viewer, wherein the pictorial display 405 is preferably a savanna-type landscape of open spaces, interspersed with distinct spread apart elements such as trees or bodies of water, to create relaxation and to reduce stress of the person.

Support structures 403 are attached to the viewer's bed 402 for ready removal of the apparatus 401 with visual display member 404 to and from the bed.

For a bed mounted unit 401, each support structure 403 supports cylindrical housing 409, which includes a top handle 406 for pulling the cylindrical housing for visual display member 404 up on telescopic poles 407 and 408, which poles 407 and 408 extend vertically upward, with the housing cylinder 409 supported at top ends thereof.

There are also separate handles 410 for pulling pictorial displays 404 or 412 downwards. The pictorial displays 404 and 412 are modular and interchangeable within housing cylinder 409. Visual displays 404 and 412 snap into quick release points on each side of housing cylinder 409, which may have half walls on 413, 414 on either end to serve as mounting points for visual display members 404 and 412, which are mounted side by side inside the bed mounted housing cylinder 409.

As shown in FIG. 4, an alternative embodiment has a vertically oriented 'scroll'-type arrangement 501, wherein support structures 503 support two upwardly extending posts 507, 508 for displaying visual display member 504 with landscape display 505 thereon. Vertically-oriented housing cylinders 509 and 510 extend up from support structures 503.

Figure 5:
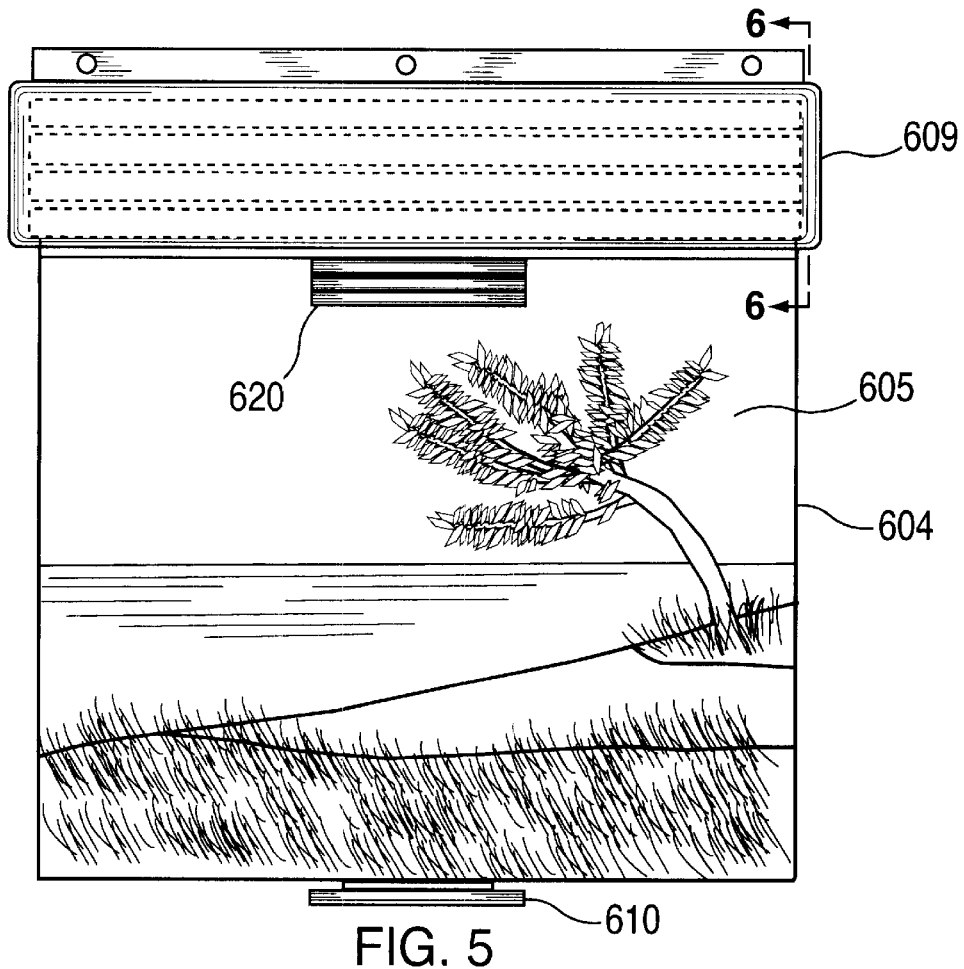
FIG. 5 is a front elevational view of an alternate wall mounted embodiment; and, FIG. 6 is a cross sectional view, taken along lines "6—6" of FIG. 5.
Figure 6:
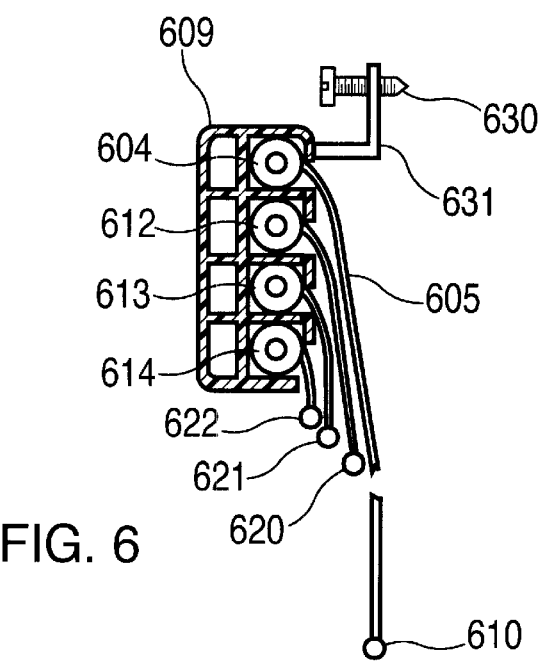

In a wall-mounted unit as shown in FIGS. 5 and 6 a plurality of pictorial displays 604, 612, 613, 614 are held in place within a housing 609. Handles 610, 620, 621, 622 are for pulling pictorial displays 603, 612, 613, 614 downwards.

Another handle 606 is for pulling pictorial displays 604, 612, 613, 614 downwards, for exposing a biophilic image, such as biophilic image 605, to the viewer. A wood screw 630 attaches through fastener bracket 631 to a wall (not shown).

Figure 7:
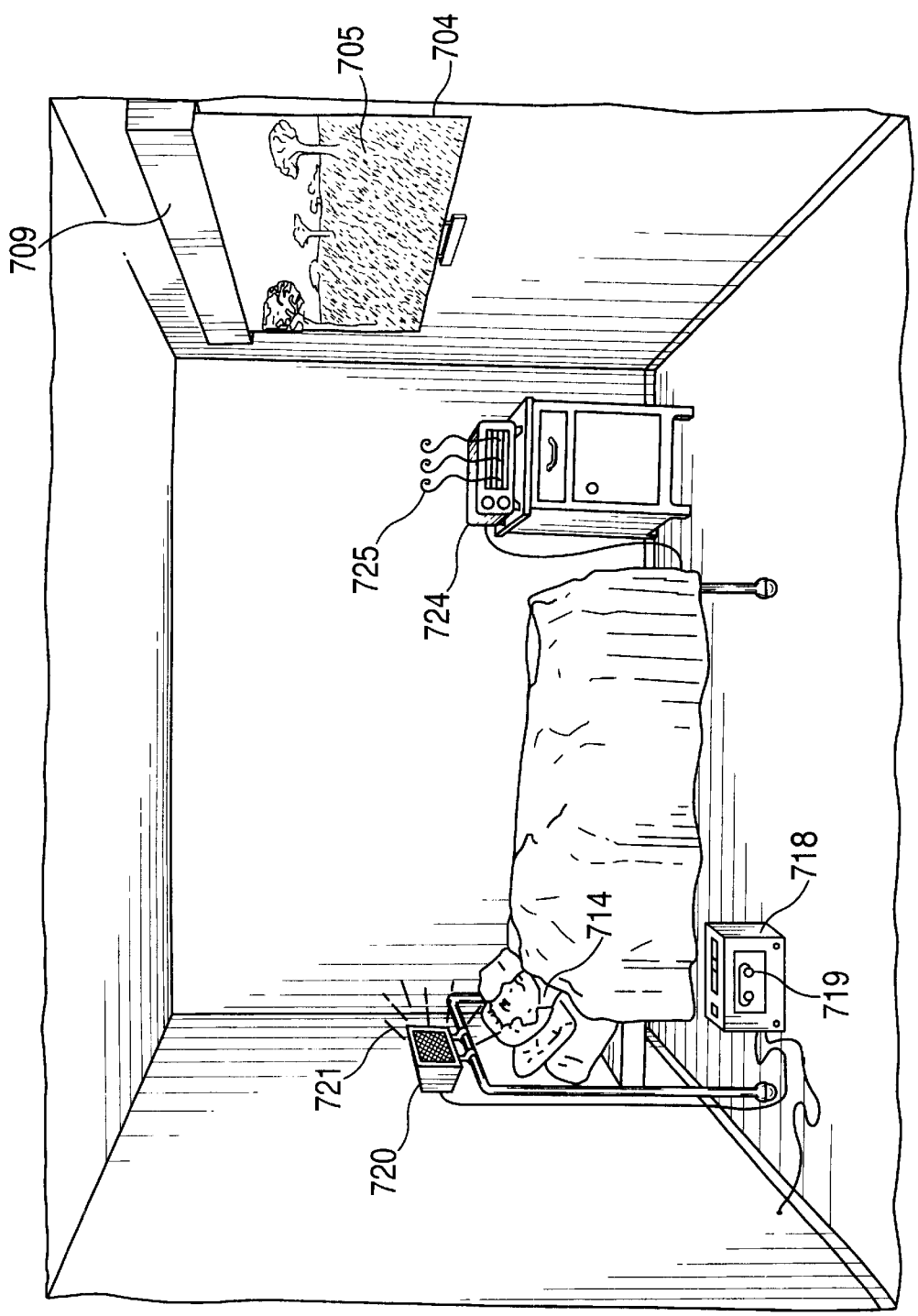
FIG. 7 is a perspective view of another embodiment.

Alternatively, as shown in FIG. 7, additional optional embodiments for a person 714 viewing a biophilic scene 705 upon a visual display 704 from a housing container 709, include complementary audio recordings 721 of biophilic sounds from audio speaker 720, which are appropriate to the visual display, such as gently falling water or chirping birds, may be provided from a sound emitting device 718, such as a compact disc player or audio cassette tape player, having a playable sound recording 719, such as a compact disc or audio cassette. Still another embodiment shown in FIG. 7 includes optionally providing aromatic scents 725 from a scent emitting device 724, that are appropriate to the biophilic landscape scene 705 of visual display 704.

It is further known that other modifications can be made to the present invention within the scope of the present invention.

I claim:

1. An apparatus for promoting personal relaxation and reducing stress in an environmentally stressful setting, such as a hospital room, for use with and in combination with a bed adapted to support a person, comprising:
   at least one support structure attached to the bed;
   said support structure attachable to a bed frame of the bed,
   at least one rollable visual display member being mounted within a cylindrical container, said at least one visual display member being a pictorial landscape of open spaces, interspersed with distinct spread apart elements including at least one group of trees and bodies of water, to create relaxation and to reduce stress of the person;
   said at least one visual display member being located so that when said rollable visual display member is unfurled from within said cylindrical container, said at least one visual display member is visible in the vicinity of the bed within the line of vision of said person in said bed.

2. The apparatus as in claim 1 wherein said at least one visual display is a plurality of visual display members.

3. The apparatus as in claim 2 wherein said visual displays are modular and interchangeable within said cylindrical container.

4. The apparatus as in claim 3 wherein said cylindrical container includes partial walls to serve as mounting points for said visual display members, which are mounted side by side inside said cylindrical container.

5. The apparatus as in claim 1 wherein said at least one visual display member is a savanna-type landscape of open spaces, interspersed with distinct spread apart elements such as trees or bodies of water, to create relaxation and to reduce stress of the person.

6. The apparatus as in claim 1 wherein said support structures are attached to the viewer's bed by quick release fasteners for ready removal of the apparatus to and from the bed.

7. The apparatus as in claim 1 wherein said cylindrical housing includes a top handle for pulling the cylindrical housing for said at least one visual display member up and down upon telescopic poles clamped to and extending up from said support structure at a foot of said bed, which said poles extend vertically upward, said housing cylinder being supported at top ends thereof.

8. The apparatus as in claim 7 further comprising at least one separate handle for pulling said at least one visual display up or down.

9. The apparatus as in claim 1 wherein said at least one visual display is rollable vertically.

10. The apparatus as in claim 1 wherein said at least one visual display is rollable horizontally.

11. The apparatus as in claim 10 wherein there are a pair of support structures comprising upwardly extending posts for displaying said at least one visual display thereon.

12. The apparatus as in claim 1 further comprising a sound emitting device providing biophilic sounds.

13. The apparatus as in claim 1 further comprising an aromatherapy emitting device providing aromas.

14. An apparatus for promoting personal relaxation and reducing stress in an environmentally stressful setting, such as a hospital room, comprising:
   at least one support structure adapted to be attached to a wall;
   at least one rollable visual display member being mounted within a cylindrical container mounted on said support structure,
   said container housing said at least one rollable visual display member being located so that when said rollable visual display member is unfurled from within said cylindrical housing, said at least one rollable visual display member is visible in the vicinity of the line of vision of the viewer, said display member having a side facing said viewer and containing a landscape of open spaces, interspersed with distinct spread apart elements such as trees or bodies of water, to create relaxation and to reduce stress of the viewer.

15. The apparatus as in claim 14 further comprising a plurality of pictorial displays being held in place within said housing.

16. The apparatus as in claim 14 further comprising a sound emitting device providing biophilic sounds.

17. The apparatus as in claim 14 further comprising an aromatherapy emitting device providing aromas.

18. An apparatus for promoting personal relaxation and reducing stress in an environmentally stressful setting comprising:
   a room containing an article of furniture adapted to support a person;
   said room having a support structure facing said article of furniture within the room;
   a rollable visual display member being mounted within said support structure;
   said visual display member being located so that when said rollable visual display member is unfurled from within said support structure, said visual display member is visible in the vicinity of said article of furniture within the line of vision of said person;
   said visual display member having a pictorial display on a surface facing said person;
   said pictorial display being of a landscape containing imagery designed to create relaxation and reduce stress of said person; wherein said display includes biophilic landscape imagery suggesting environments in which the evolutionary differentiation of Homo sapiens from ancestral paleoanthropopids is believed to have occurred,
   wherein further said biophilic landscape imagery includes imagery of vegetation dominated by a relatively low herbaceous understory and a relatively widely spaced tree canopy; and,
   means for attaching and permitting ready removal of said visual display member to and from said support structure.

19. An apparatus for promoting personal relaxation and reducing stress in an environmentally stressful setting comprising:
   a room containing an article of furniture adapted to support a person;
   said room having a curtain facing said article of furniture within the room;
   said curtain being an unframed, freely suspended visual display member of fire retardant fabric construction to eliminate glare, said curtain being suspended from a curtain support rod;
   said visual display curtain member being located so that said visual display curtain member is visible in the vicinity of said article of furniture within the line of vision of said person;
   said visual display curtain member having a pictorial display on a surface facing said person;
   said pictorial display being of a landscape containing imagery designed to create relaxation and reduce stress of said person;

said display being produced on said fire retardant fabric by a high resolution sublimation printing process resulting in said display and fire retardant fabric being washable and durable to heated washing standards of 160 degrees F. so that any infectious organisms thereon are eradicated.

20. An apparatus for promoting personal relaxation and reducing stress in an environmentally stressful setting comprising:

a room containing an article of furniture adapted to support a person;

said room having a curtain facing said article of furniture within the room;

said curtain being an unframed, freely suspended visual display member of fire retardant fabric construction to eliminate glare; said curtain being suspended from a curtain support rod;

said visual display curtain member being located so that said visual display member is visible in the vicinity of said article of furniture within the line of vision of said person;

said visual display curtain member having a pictorial display on a surface facing said person;

said pictorial display being of a landscape containing imagery designed to create relaxation and reduce stress of said person; wherein said display includes biophilic landscape imagery suggesting environments in which the evolutionary differentiation of Homo sapiens from ancestral paleoanthropids is believed to have occurred, wherein further said biophilic landscape imagery includes imagery of vegetation dominated by a relatively low herbaceous understory and a relatively widely spaced tree canopy.

21. In combination with a bed for promoting personal relaxation and reducing stress comprising:

a collapsible support structure removably attached to a frame of said bed;

a cylindrical container mounted on said support structure so that said cylindrical container adjoins said frame when said support structure is collapsed and in a display position away from said frame when said support structure is extended;

a visual display member coiled within said cylindrical container; and means for unfurling said visual display member visible to a person in said bed when said support structure is extended into said display position, said visual display member having on a side facing the person in said bed a nature scene capable of stimulating relaxation and restorative response in said person.

22. The combination of claim 21 in which said nature scene comprises a glare free spatially open serene natural setting.

23. The combination of claim 22 in which said natural setting includes a tranquil water body.

24. The combination of claim 23 in which said natural setting includes a wide sky portion beginning along and extending above a distant horizon line and vegetation comprising substantially herbaceous understory of plant life under a relatively open canopy formed by at least one of substantially widely spaced trees and tree clusters.

* * * * *